United States Patent [19]

Tanouchi et al.

[11] 4,201,871

[45] May 6, 1980

[54] PROCESS FOR RECOVERING TEREPHTHALIC ACID

[75] Inventors: Masatoshi Tanouchi; Hiroshi Takeuchi; Kazuki Ban; Yoshiyuki Asahina, all of Nobeoka, Japan

[73] Assignee: Asahi Kasei Kogyo Kabushiki Kaisha, Osaka, Japan

[21] Appl. No.: 14,216

[22] Filed: Feb. 22, 1979

[30] Foreign Application Priority Data

Feb. 23, 1978 [JP] Japan .................. 53-20225
May 27, 1978 [JP] Japan .................. 53-63474
Dec. 26, 1978 [JP] Japan .................. 53-159274

[51] Int. Cl.² .............................................. C07C 51/42
[52] U.S. Cl. ................................................. 562/486
[58] Field of Search ............................... 562/485, 486

[56] References Cited

U.S. PATENT DOCUMENTS 3,853,924  12/1974  Meyer et al. ................ 562/486

*Primary Examiner*—Alan Siegel
*Attorney, Agent, or Firm*—Armstrong, Nikaido, Marmelstein & Kubovcik

[57] ABSTRACT

This invention relates to an improved process for recovering highly pure terephthalic acid crystals from a suspension containing terephthalic acid product obtained by the liquid phase oxidation of para-substituted aromatic compounds in the presence of oxidizing catalyst. The improvement comprises bringing said suspension into continuous countercurrent contact with ascending hot acetic acid containing water in a single tower under the conditions of specified temperature, specified ascending rate of the acetic acid containing water and specified residence time of the suspension, to replace the mother liquor of the suspension with said acetic acid, and recovering the mother liquor as an overflow, while recovering terephthalic acid as an underflow in the form of suspension of highly purified crystals and, if necessary, allowing the suspension to stay in a stirring tank.

23 Claims, 4 Drawing Figures

FIG. 2A (UNIT: mm)
ELEVATION

PLAN

PLAN even small amount of impurities, such as oxidation intermediates, is unfavorable because such impurities causes lowering of polymerization rate or discoloration of polymer.

PROCESS FOR RECOVERING TEREPHTHALIC ACID

BACKGROUND OF THE INVENTION

1. Field of the Invention

This invention relates to a process for producing terephthalic acid, which comprises oxidizing in the liquid phase in acetic acid a para-substituted aromatic compound with a gas containing molecular oxygen in the presence of oxidizing catalyst to obtain a reaction mixture in the form of a suspension containing terephthalic acid, and recovering the terephthalic acid crystals from said suspension, and more particularly relates to a process for said recovering.

2. Description of the Prior Art

In a typical known process for producing terephthalic acid, a para-dialkylbenzene, for example, is oxidized in acetic acid, used as solvent, with molecular oxygen in the presence of a catalyst. The para-dialkylbenzene generally used is para-xylene and the catalyst generally used is a cobalt compound and a manganese compound. An oxidation promoter such as a bromine compound, methyl ethyl ketone, paraldehyde or acetaldehyde is occasionally used. When para-xylene is oxidized in the liquid phase in acetic acid, used as solvent, and in the presence of a catalyst, the product terephthalic acid, being very difficultly soluble in acetic acid, crystallizes out of the solvent acetic acid, forming a suspension. The suspending medium, that is, the acetic acid contains a small amount of terephthalic acid dissolved therein, catalyst, unreacted para-xylene, intermediate oxidation products such as para-tolualdehyde, para-toluic acid, 4-carboxybenzaldehyde, and the like, an oxidation retarder such as para-cresol, and other organic impurities which cause discoloration. The main technical problems in recovering terephthalic acid from such an oxidation reaction mixture, that is, the suspension of terephthalic acid, arise from the following facts:

(1) Coprecipitation of dissolved impurities in the course of crystallization of dissolved terephthalic acid from the oxidation reaction mixture by cooling.

(2) The terephthalic acid crystals in the oxidation reaction mixture, i.e. a hot suspension of terephthalic acid, have a broad particle size distribution and the smaller the particle size is, the larger is the impurity content of crystals. Minute crystals which precipitate on cooling the suspension have also a larger impurity content.

(3) Coarse crystals in the terephthalic acid suspension also contain impurities.

Several methods had heretofore been proposed for recovering terephthalic acid from the suspension obtained as the oxidation reaction mixture, including those disclosed in Japanese Patent Publication No. 8,818/64 (A process for recovering crystals by gradually cooling the suspension taking long residence time by means of using several crystallizing tanks), Japanese Patent Publication No. 34,023/71 (A process comprising precipitating terephthalic acid by mixing with low temperature carboxylic acid solvent), Japanese Patent Application Laid-open ("Kokai") No. 135,939/74 (A process comprising separating terephthalic acid and mother liquor from reaction mixture at a temperature close to the reaction temperature) and Japanese Patent Application Laid-open ("Kokai") No. 91,835/77 (A process comprising additionally oxidizing the terephthalic acid suspension by molecular oxygen). Although each of the proposed methods solved the above problems to some extent, none was successful in solving all of the problems prior to the accomplishement of this invention.

The product terephthalic acid, which was produced according to the conventional method and subjected to solid-liquid separation and drying, has not satisfactory quality and requires further purifying treatment such as washing in order to obtain terephthalic acid pure enough for direct polymerization, and thus, these methods are complicated in steps and apparatus.

On the other hand, Japanese Patent Application Laid-open ("Kokai") No. 9,736/78 discloses a method in which the reaction mixture mother liquor is replaced with acetic acid at high temperatures by using a multistage cyclone unit and other means to separate the reaction mixture into a suspension of larger crystals in fresh acetic acid and mother liquor containing smaller crystals, the latter of which being recycled back to the reaction system. This is a common place but good method for solving the aforementioned problems of (1) and (2). However, it requires a complicated unit consisting of at least three stages of equipments (for example, cyclones) connected in series and is complicated also in operation. Moreover, it requires a large quantity of cold acetic acid for dilution so that the significant amount of impurities contained in the resulting suspension of larger crystals in fresh acetic acid may remain in the mother liquor without precipitating on being rapidly cooled and that the suspension may be cooled by the addition of fresh acetic acid. As is apparent from the foregoing description, none of the conventional methods is satisfactory and the fact is that in order to obtain highly pure terephthalic acid suitable for use in direct polymerization for production of so-called fiber-grade polyester, it is unavoidable to subject the crystallized terephthalic acid to an additional treatment using complicated equipments and complicated procedures.

OBJECT OF THE INVENTION

An object of this invention is to provide a commercially advantageous improved method for recovering highly pure terephthalic acid crystals from a suspension containing terephthalic acid, which suspension is obtained as reaction mixture by the liquid-phase oxidation of a para-substituted aromatic compound in acetic acid in the presence of an oxidizing catalyst.

SUMMARY OF THE INVENTION

The present inventors found a surprising fact that so-called direct polymerization-grade terephthalic acid is obtained directly from the suspension by a simple method which comprises bringing a stream of the oxidation reaction mixture in the form of suspension containing terephthalic acid crystals into slow continuous countercurrent contact with a stream of hot acetic acid containing water in a single tower, while maintaining the fluid in the tower at a temperature at which no more precipitation of terephthalic acid will take place, and separating terephthalic acid crystals from the effluent suspension.

The present inventors advanced further detailed studies on the type of equipment which exhibits excellent continuous countercurrent contact effect and on the conditions of operating such an equipment. As a result, it was found that it is possible to recover highly pure direct polymerization-grade terephthalic acid in the form of slurry in acetic acid containing water, containing substantially no impurities initially present in the reaction mixture and without being contaminated with any impurity in conventional after-treatments of the reaction mixture, by using a washing tower, which is actually a settling tower of simple structure, and bringing the reaction mixture suspension into continuous and slow countercurrent contact with hot aqueous acetic acid, while maintaining the fluid temperature, ascending velocity of acetic acid containing water, and residence time of the crystals within specified ranges. Such a success achieved by using such a simple procedure is epoch-making and, moreover, all of the technical problems mentioned before can be solved by this simple procedure.

It was further found that terephthalic acid of a still higher quality can be obtained by allowing the suspension of terephthalic acid crystals in hot acetic acid containing water from the continuous countercurrent contacting tower to stay in a stirring tank without any other treatment, while maintaining the temperature and residence time within specified ranges. The effect of the above treatment is a stirring tank on the improvement of quality is greater than the effect obtained by prolonged residence time in the continuous countercurrent contact tower. The above treatment can be carried out in a common stirring tank of simple structure and contributes to a reduction in length and/or diameter of the contact tower, resulting in reduced investment and improved operation. Thus, the efficiency and economics of the process for washing by the replacement of mother liquor with acetic acid containing water were markedly improved, leading to the accomplishment of this invention.

According to this invention, there is provided an improvement in a process for recovering highly pure terephthalic acid crystals, which process comprises subjecting a para-substituted aromatic compound to liquid phase oxidation with a gas containing molecular oxygen in acetic acid in the presence of an oxidizing catalyst, at a reaction temperature of 100° to 250° C., while maintaining the water content of the reaction system within the range of 2 to 15% by weight based on said acetic acid, to obtain a reaction mixture in the form of suspension containing terephthalic acid, and recovering highly pure terephthalic acid crystals from said suspension; said improvement, whereby highly pure terephthalic acid crystals for use in direct polymerization are recovered, comprises feeding said suspension, without being subjected to cooling and solid-liquid separation, to a single tower, bringing the fed suspension into continuous countercurrent contact with acetic acid containing water in the tower, while maintaining the fluid temperature at a temperature not lower than the oxidation temperature by more than 10° C., the ascending speed of said acetic acid containing water within the range of 0.005 to 5 cm/second, and the average residence time of terephthalic acid crystals in the tower at 30 seconds or more, to replace the mother liquor in said suspension with the acetic acid containing water in countercurrent contact with the suspension, recovering said mother liquor as the ascending stream, while collecting highly purified terephthalic acid crystals in the descending stream in the form of suspension, and, if necessary, allowing said descending stream of suspension to stay in a stirring tank, while maintaining the temperature of the suspension at a temperature not lower than the temperature in the tower by more than 10° C.

As described above, a surprising countercurrent contact effect was obtained in a simply constructed tower by maintaining the fluid temperature in the tower, ascending speed of acetic acid containing water and residence time of crystals within suitable ranges. Further, by an additional simple treatment of keeping the purified suspension from the tower to stay in a stirring tank, while maintaining the temperature and residence time of crystals within suitable ranges, it has now become possible to enhance the purification effect and to reduce the size of tower to more commercially practicable scale. The development of such a successful method for the terephthalic acid recovery is unexpectable from the viewpoint of prior technique and would certainly be a decisive step toward the ideal technique long hoped for in the related field.

The invention is more fully described below.

DESCRIPTION OF THE PREFERRED EMBODIMENTS

In the process of this invention, the suspension of terephthalic acid crystals produced by the liquid phase oxidation and fed to the tower should be maintained at a temperature not lower than the oxidation temperature by more than 10° C. until the continuous countercurrent contact with hot acetic acid containing water has been terminated. If the temperature of the suspension is decreased by more than 10° C., terephthalic acid dissolved in mother liquor will be precipitated, whereby coprecipitation of the impurities contained in the mother liquor will take place, resulting in increased proportion of impure crystals which are detrimental to the merits of this invention; blocking of the feed line of the suspension; and increased build-up on the tower wall. Although there is no upper limit of the temperature in the tower, a preferable temperature is that of the oxidation, because further precipitation of terephthalic acid crystals can be avoided and additional heating is unnecessary.

The continuous countercurrent contact as herein referred to is realized by keeping the ascending velocity of the acetic acid containing water and the residence time in tower of crystals within the ranges as defined hereunder. The countercurrently ascending velocity (linear velocity) of acetic acid containing water should be in the range of 0.005 to 5 cm/second, preferably 0.01 to 0.5 cm/second. If the velocity is below 0.005 cm/second, the removal of more impure finer crystals by the ascending stream becomes difficult and, in addition, satisfactory countercurrent contact effect becomes difficult to obtain. If the ascending velocity exceeds 5 cm/second, the purity of the recovered terephthalic acid crystals becomes inferior and satisfactory purification cannot be attained even if treated in the stirring tank subsequent to the tower treatment; in addition, the crystals obtained are no more suitable for use in the direct polymerization for the following reason:

In the step of esterification of crystalline terephthalic acid with ethylene glycol, the suspension of the crystals in ethylene glycol (this suspension is referred to as slurry) must be of sufficient fluidity. The ability of crystalline terephthalic acid to produce an acceptable slurry is frequently expressed in terms of the molar ratio of ethylene glycol to terephthalic acid in a slurry having a viscosity of 30 poises. A preferred molar ratio is said to be 1.1–1.2. Since the size and shape of the crystals are believed to affect said ratio, a crystalline terephthalic acid of large and uniform crystal size and uniform crystal shape is preferred. The crystalline terephthalic acid obtained at an ascending velocity of acetic acid containing water exceeding 5 cm/second is poor in slurry-forming ability, and thus, an excess of ethylene glycol is required to obtain a slurry of acceptable fluidity and, in addition, the excess ethylene glycol is subject to a side reaction, resulting in a loss of ethylene glycol.

Although the exact reason for the inferior slurry-forming ability of such a crystalline terephthalic acid is not apparent, it is probably due to breakdown of crystals induced by the collision of crystals with one another. At an ascending velocity as high as 5 cm or more per second, the overflow from the tower becomes markedly diluted in catalyst content with acetic acid containing water and, hence, must be concentrated or treated otherwise before being recycled back to the oxidation reactor to serve as reaction medium. Such an additional treatment causes an extra cost. The higher ascending velocity requires more acetic acid containing water not replenishable with the condensate (described later) obtained from the reaction mixture; and even larger terephthalic acid crystals tend to be carried away.

The residence time of terephthalic acid crystals in the countercurrent contact zone should be 30 seconds or more. Terephthalic acid obtained with a residence time of at least 30 seconds has a purity sufficient for use in producing common polyesters. However, when a highly pure product such as fiber-grade polyester, for example, that having a color of 10 APHA or less and an impurity 4-carboxybenzaldehyde content of 500 ppm or less is needed, a residence time in tower of two minutes or more or further treatment in the stirring tank subsequent to the tower treatment is preferable. The degree of purification by the single tower treatment begins to level off at a residence time of about 30 minutes and remains unchanged beyond one hour which, therefore, is the upper limit. A longer residence time brings about merely a decrease in the tower output and, hence, is uneconomical. Below the upper limit, a longer residence time improves more the quality of terephthalic acid crystals. However, in order to increase the residence time in the tower while maintaining a given tower output, it is necessary to use a tower of larger diameter or preferably increased height, resulting in increased bulkiness of the tower and some degree of difficulty in operation. From an economical point of view, the favorable effect of prolonged residence time is better secured by the joint use of a continuous countercurrent contact tower and a stirring tank. The operation in this case is such that the mean residence time of terephthalic acid crystals in the tower is reduced to a relatively short period of 30 seconds to 10 minutes, preferably 30 seconds to 2 minutes and the effluent terephthalic acid suspension from the tower is allowed to stay in the stirring tank for a suitable period of time, while being maintained at a temperature not lower than the temperature in the tower by more than 10° C.

Although the residence time in the stirring tank can be reduced to some extent by prolonging the residence time in the continuous countercurrent contact tower, such a mode of operation is not always beneficial because of the accompanying disadvantages such as an increase in tower size.

When the residence time is 2 minutes or less, the tower size is quite small and so is the investment. Modifications in equipments such as integration of the continuous countercurrent tower and the stirring tank by connecting both in series are possible without sacrificing the advantages of this invention so long as the operation conditions are kept unchanged.

When the residence time in the tower is more than 2 minutes, the stirring tank may be occasionally dispensed with depending on a quality required for the product. However, even in this case, joint use of both equipments is, of course, advantageous for further improvement in the product quality.

The continuous countercurrent contact according to this invention imposes no particular limitation on the mode of feeding the oxidation reaction mixture in the form of terephthalic acid suspension to the countercurrent contact tower and on the mode of withdrawing the recovered terephthalic acid suspension. The feeding and withdrawing can be continuous, semi-continuous or intermittent. The important point is whether or not the continuous countercurrent contact is effected in a single tower under the aforementioned two necessary conditions of specified ascending velocity of acetic acid containing water in the tower and the specified residence time of terephthalic acid crystals in the tower. So long as the said two necessary conditions are fullfilled, it is possible to charge the suspension either continuously or intermittently before beginning of the continuous countercurrent contact and likewise it is possible to withdraw the suspension in any way after termination of the continuous countercurrent contact. For instance, the advantages of this invention can be secured by repeating the following sequence of batchwise operation steps: (a) feeding of the reaction mixture to the tower, (b) interruption of the feeding, (c) effecting the continuous countercurrent contact by the continuous feeding of acetic acid containing water and continuous discharge of the effluent as overflow, (d) interruption of the continuous countercurrent contact operation, and (e) flash discharge of the terephthalic acid suspension in acetic acid containing water produced by the continuous countercurrent contact treatment in step (c). It is needless to say that it is a good way to carry out simultaneously the feeding and the discharge, thereby to operate the whole process in a completely continuous way.

In order to ensure the continuous countercurrent contact under the aforementioned conditions, it is preferable to introduce the reaction mixture suspension into a vertical tower of appropriate height at the top and introduce acetic acid containing water from the bottom. Customary chemical engineering means for promoting the countercurrent contact can be utilized.

One of the reasons for operating the continuous countercurrent contact tower under the specified conditions is to minimize the oxidation mother liquor content of the water-containing acetic acid suspension obtained from the bottom of the contact tower. Although the less the said mother liquor content is, the higher will be the purity of recovered terephthalic acid, even when the mother liquor content amounted to about 20% by weight, sufficient purification can be achieved by allowing the effluent suspension from the tower to stay in the stirring tank. If the stirring tank is not available, the mother liquor content of the effluent suspension is preferably reduced to about 10% by weight.

One of the ways to improve the mother liquor replacement is to maintain the abovesaid operation conditions within a most favorable range. Another way is to use a higher tower or to prolong the residence time of terephthalic acid until a desired replacement has been attained. A more effective way is to provide the tower with at least one, preferably 5 or more, perforated trays each having a total of 5 to 50% (based on crosssectional area of the tower) of aperture area. While the shape of aperture can be circular, rectangular, or of any other form, each aperture should have a minimum clearance of 5 mm. The shape of each tray can be horizontal platelike. If it is desired to avoid deposition of terephthalic acid crystals on the horizontal plate, tray can be of inclined structure to lead the crystals to the aperture, the inclination being greater than the angle of repose of the crystals. To increase the efficiency of countercurrent contact, it is preferable to provide a large number of perforations, 1 to 3 mm in diameter, distributed all over the inclined part of the tray to disperse the ascending water-containing acetic acid. By such or other simple means, it is possible to improve the efficiency of countercurrent contact and, in its turn, the replacement. It is easy enough to attain a replacement of even 99.5% or higher with a contact tray tower of a markedly smaller size as compared with a tower provided with no tray. If the replacement is insufficient, it is necessary to prolong the residence time in the stirring tank to attain a given degree of purification.

The descending stream obtained from the countercurrent contact tower is a suspension of terephthalic acid crystals in acetic acid containing water of low impurity content. A mode of the residence of the suspension in tower or stirring tank can be either continuous or batchwise. In the case of continuous operation, the residence time should be prolonged to some extent as compared with the case of batchwise operation. The temperature in the stirring tank is preferably not lower than that of the countercurrent contact by more than 10° C. and the upper temperature limit is 225° C. Although a higher temperature up to 225° C. is preferred, terephthalic acid crystals tend to be deteriorated in color at too high temperature. It would be economical to maintain the temperature close to that in the contact tower, because then additional heating is almost unnecessary. The suitable residence time in the stirring tank is 5 to 180 minutes. To improve the purification effect in the stirring tank, it is a way to add, to the fed suspension of terephthalic acid in acetic acid containing water obtained from the continuous countercurrent contact tower, fresh hot acetic acid containing water in an amount of about 50 to about 300% by weight based on original acetic acid containing water present in the suspension.

The reason for the remarkable purification effect obtained by allowing the suspension of terephthalic acid crystals to stay in the contact tower or stirring tank seems to be that in said suspension, terephthalic acid crystals are suspended in acetic acid containing water of low impurity content, because it is obtained by replacing the oxidation mother liquor with acetic acid containing water under such conditions that no more fresh crystals will be precipitated; and during the stay, the impurities within the crystals are sufficiently extracted. The degree of purification attained by subjecting the suspension to extractive treatment without prior cooling and solid-liquid separation is unexpectedly high and indeed far higher beyond comparison than that obtained by the customary method widely employed at present, in which the crude crystals separated by cooling the suspension are washed with acetic acid containing water at an elevated temperature. This seems to be due to the difference between the crystals immediately after reaction and those after cooling in permeability into the crystals of acetic acid containing water which serves as washing solution and in diffusion velocity of impurities within the crystals resulting from the difference in distribution of impurities in the crystals and porosity of the crystals. Furthermore, one of the other advantages of this invention is an improved slurry-forming ability of the product terephthalic acid owing presumably to the stirring effect which rounds off the crystals during the stay in the stirring tank.

The acetic acid containing water used in this invention contains preferably 10 to 20% by weight of water and, of course, can be prepared by diluting acetic acid with water. However, it is to be noted that when the condensate of 10 to 20% water content obtained from the vapor generated during oxidation is used in the continuous countercurrent contact step, a better purification effect is obtained over the above range of water content than that obtained by using acetic acid containing water prepared by dilution. Although the reason is not yet to be elucidated, such a difference seems to relate somehow to the presence of methyl acetate, paraxylene, formic acid, acetaldehyde, formaldehyde, and the like, in the condensate.

The remarkable advantages of this invention cannot be expectable from the disclosure of Japanese Patent Application Laid-open ("Kokai") No. 9,736/78. In the hydrocyclones disclosed in said Application, both feeds of fresh aqueous acetic acid and the reaction mixture are carried out by a parallel flow system, in which the both are mixed together. Consequently, it seems that for this reason there are required a unit of series connected hydrocyclones of at least 3 stages, as described in the upper left column, p. 269 of the specification of said No. 9,736/78, and a large quantity of cold acetic acid. To the contrary, according to this invention, substantially pure terephthalic acid crystals having a satisfactory slurry-forming ability are recovered by a simple procedure of carrying out the motor liquor replacement for a relatively long period of time in a single tower of simple structure or carrying out the replacement for a short period of time and then allowing the resulting suspension to stay in a simple stirring tank. The choice between said two types of procedure depends on the conditions for oxidation and the required purity of the product.

Since the contamination of terephthalic acid in the reaction mixture with the impurities in the mother liquor and the contamination due to co-precipitation of impurities at the time of crystallization of dissolved terephthalic acid are proportional to the concentration of impurities in the reaction mixture, it is desirable to reduce said concentration of impurities. For this purpose it is desirable to select suitable reaction conditions under which oxidation proceeds most actively.

The oxidizing catalyst in heavy metal compounds, among which cobalt compounds and manganese compounds are preferred. A cobalt-manganese-bromine combination is known to be a desirable catalyst system. Suitable compounds of cobalt and manganese are those soluble in acetic acid, such as, for example, acetates and naphthenates. The suitable amount of a metal compounds in terms of metal based on acetic acid is 0.01 to 0.5%, preferably 0.02 to 0.2% by weight for a cobalt compound and 0.005 to 0.2%, preferably 0.01 to 0.1% by weight for a manganese compound. The weight ratio of cobalt compound to manganese compound is not critical. Suitable bromine sources are hydrobromic acid, cobalt bromide, manganese bromide, sodium bromide, potassium bromide, and bromoacetic acid. Suitable amount of bromine compound in terms of bromine atom based on acetic acid is 0.08% or more, preferably 0.1 to 0.5% by weight. Of the bromine sources, hydrobromic acid is preferred. If necessary, promoters such as $C_{1-3}$ aliphatic alcohols, $C_{1-3}$ aliphatic aldehydes or $C_{3-5}$ aliphatic ketones can be present in the reaction system. Preferred promoters are acetaldehyde, methanol and methyl ethyl ketone. The reaction temperature is 100° to 250° C., preferably 170° to 220° C. The reaction pressure is that sufficient for keeping the solvent in the liquid phase. The reaction can be carried out continuously or batchwise. The feeding of the starting materials and the discharge of the product are preferably conducted continuously.

DESCRIPTION OF THE PREFERRED EMBODIMENT WITH REFERENCE TO DRAWINGS

One embodiment of the invention is illustrated below with reference to accompanying drawings.

Figure 1:
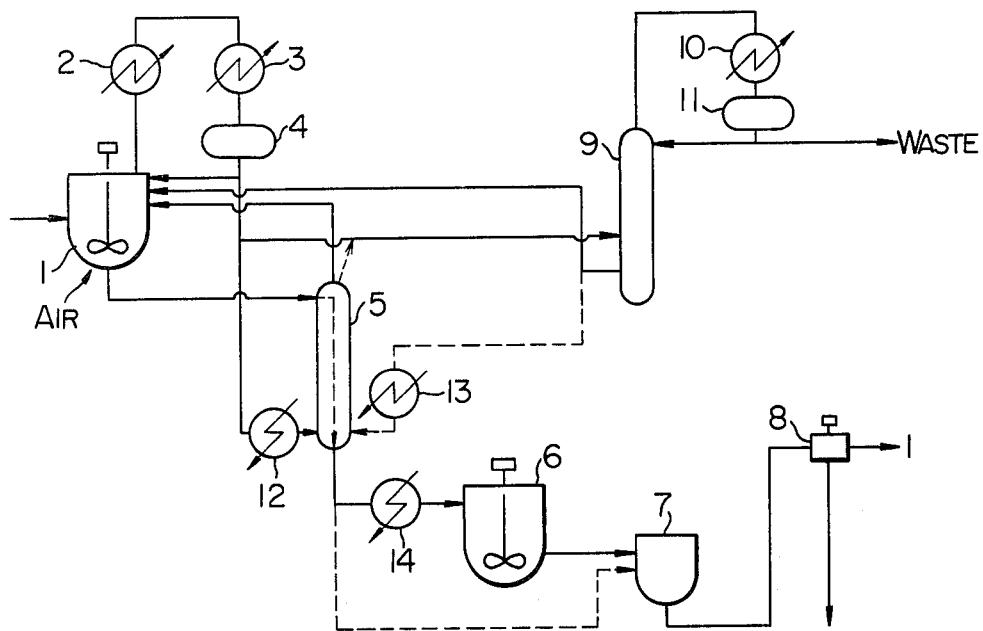
FIG. 1 is a flow sheet which shows an example of the embodiment of this invention.
Figure 1:
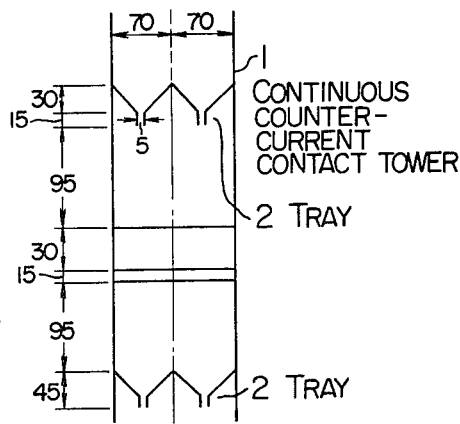

In FIG. 1, 1 is oxidation reactor; 2 is main condenser for the vapor from the top of reactor; 3 is auxiliary condenser; 4 is condensate receiving tank; 5 is continuous countercurrent contact tower of this invention; 6 is stirring tank; 7 is flash tank; 8 is solid-liquid separator; 9 is acetic acid distillation dehydration tower; 10 is condenser; 11 is condensate receiving tank; and 12, 13 and 14 are preheaters. A terephthalic acid suspension obtained by liquid-phase oxidation is fed from reactor 1 to the top of single tower 5, while maintaining the feed at a temperature not lower than the reaction temperature by more than 10° C. Hot acetic acid containing water from acetic acid distillation dehydration tower 9 is fed via preheater 13 to the bottom of tower 5. In tower 5, the suspension and the acetic acid containing water are brought into countercurrent contact, while maintaining the above-said temperature. The residence time of the terephthalic acid crystals in the countercurrent zone is 2 minutes or more. In case the stirring tank 6 is used to hold the suspension from tower 5 for further purification, the residence time in tower 5 is 30 seconds to 10 minutes, preferably up to 2 minutes. The hot acetic acid containing water to be fed to tower 5 is adjusted to a water content of 10 to 20% by weight. It is economical to utilize a water-containing acetic acid condensate of vapor from the vent of reactor 1 as the countercurrent contact liquor, because preheating is scarcely needed. Since the overflow from the top of tower 5 is of substantially the same composition and temperature as those of the oxidation mother liquor in reactor 1, it can be recycled back to the reactor without any treatment. However, in order to avoid excessive accumulation of impurities including oxidation inhibitors such as paracresol which are formed by side reactions, a suitable portion of said overflow is preferably sent to the recovery and purification unit for solvents and catalyst components. The overflow also contains fine terephthalic acid crystals which serve as nuclei for the growth of crystals in reactor 1 and, hence, are recovered after all. The underflow from tower 5 is a suspension of terephthalic acid crystals in the liquid phase comprising catalyst and other impurities in very low concentrations, acetic acid, water and dissolved terephthalic acid. In case this suspension is treated in stirring tank 6, it is fed, generally as such or via preheater if necessary, to stirring tank 6 and allowed to stay therein for 5 to 180 minutes to extract effectively the remaining impurities from the crystals. If the concentration of impurities dissolved in acetic acid containing water is appreciably high, the suspension can be treated again in the countercurrent contact tower. However, it is better to avoid such a double treatment by proper selection of the conditions for oxidation and/or increasing the degree of mother liquor replacement in the countercurrent contact tower. Before feeding to stirring tank 6, the suspension from countercurrent contact tower 5 can be diluted with 50 to 300% by weight (based on the acetic acid in the suspension) of fresh hot acetic acid containing water to increase the proportion of acetic acid to the terephthalic acid crystals, thereby to enhance purification. When abundant acetic acid containing water is easily available in the system, this is an effective procedure.

The terephthalic acid crystals in so treated suspension contain very little adhered impurities. The separation of high-purity terephthalic acid crystals from the suspension presents no particular technical problem. Known techniques for solid-liquid separation can be utilized to obtain cold acetic acid and terephthalic acid from the hot suspension in acetic acid containing water. For instance, this can be accomplished by flashing the hot suspension to lower pressures or by quenching the hot suspension. Thus, highly pure terephthalic acid can be obtained without re-contamination with impurities. As shown in FIG. 1, the suspension from stirring tank 6 can be fed via transfer line to flash tank 7 where the pressure is released all at once to effect crystallization at atmospheric pressure. Alternatively, the suspension can be quenched by the addition of cold acetic acid to a temperature lower than the boiling point and discharged continuously. The suspension of terephthalic acid in acetic acid which has been cooled to a temperature lower than the boiling point of acetic acid is subjected to any known treatment for solid-liquid separation such as, for example, centrifuging or filtration. Since the mother liquor so separated still contains an equilibrium quantity of dissolved terephthalic acid at that temperature, it is preferably recycled to the reaction system to be re-used as the oxidation medium, thereby to recover the dissolved terephthalic acid.

Although the terephthalic acid crystals so obtained still contain very small amounts of impurities in the crystals, the purity is sufficient enough for the direct polymerization. Accordingly, the crystals separated from the effluent are simply dried to remove the adhered liquor to obtain the final product without being subjected to any of those aftertreatments such as washing, reconversion into slurry, and recrystallization which are necessary in conventional methods for recovering terephthalic acid. The product terephthalic acid has nothing to be complained of as to impurity content or crystal shape.

Figure 2B:
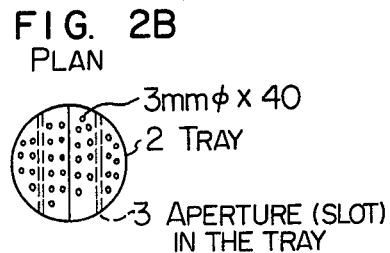
FIG. 2 is an example of the tray to be provided in the continuous countercurrent contact tower shown in FIG. 1.
Figure 2C:
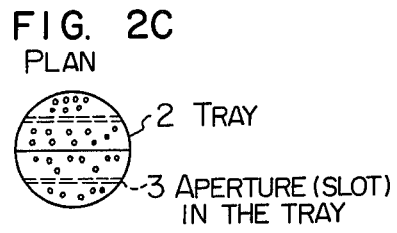

FIG. 2 of the accompanying drawings represents an example of tray provided in the aforementioned continuous countercurrent contact tower. In FIG. 2, (A) is a crosssectional side view of a continuous countercurrent contact tower provided with three trays; and (B) and (C) are plan views of the tray; 1 is continuous countercurrent contact tower wall; 2 is tray; 3 is aperture (slot)

in the tray. The trays are arranged so that the direction of apertures (slots) in each tray may be at right angles to that of apertures in the adjacent tray.

As described above, according to this invention a suspension of highly pure terephthalic acid can be obtained continuously by the simple and slow continuous countercurrent contact and the retention treatment at elevated temperatures in a stirring tank. The mother liquor recovered as the overflow from the contact tower retains original oxidation activity and can be re-used in the oxidation step. The suspension of terephthalic acid from the tower, which is the main point of this invention, is very low in impurity content and on cooling and solid-liquor separation by any method easily yields high-purity terephthalic acid crystals. Consequently, operation in the terephthalic acid recovery step subsequent to the oxidation step is simplified to a great extent as compared with conventional methods. By using the condensate available from the reaction system as the acetic acid containing water, the washing effect is further increased and the thermal energy cost will be reduced. According to this invention, in addition to the remarkable purification, a favorable modification of the crystal shape can be achieved, resulting in remarkable improvement in slurry-forming ability of the product terephthalic acid. This is also one of the important advantages of this invention.

The suspension discharged from the continuous countercurrent contact tower 5 contains little oxidizing catalyst and little bromine compound having a corrosive action which is especially strong at high temperatures. As the result, it becomes possible to utilize lower grade construction materials for the construction of stirring tank 6, cooling equipments, flash tank 7, and solid-liquid separater 8, which is an industrially important advantage of this invention.

Since it becomes possible by the method of this invention to recover highly pure terephthalic acid very easily from the oxidation reaction mixture, those reaction mixtures which contain impurities in high concentrations can also be used as starting materials for recovering direct polymerization-grade terephthalic acid. Consequently, oxidation can be conducted under mild conditions instead of severe conditions prevailing in the production of highly pure terephthalic acid for the sole purpose of reducing the impurity content. In current practice, severe conditions are maintained by selecting various reaction factors such as reaction temperature, catalyst concentration, water content of reaction system, and oxygen partial pressure so as to conduct vigorous oxidation. Under such severe conditions, oxidation reaction accommpanies loss of the reaction solvent such as acetic acid due to oxidative decomposition which is avoidable under mild conditions. It is also possible to conduct oxidation under those mild conditions which have not been in actual use on account of high impurity content of the reaction mixture.

Thus, the method of this invention, which might be called "countercurrent contact and hot retention method", is exceedingly effective in producing highly pure direct polymerization-grade terephthalic acid directly from the reaction mixture obtained by the liquid-phase oxidation of aromatic compounds such as paradialkylbenzenes. The present inventors are convinced that this invention is an important contribution to the art.

EXAMPLES

This invention will now be described in detail by reference to the following Examples that by no means limit the scope of the invention.

In Examples, the degree of coloring of terephthalic acid crystals was evaluated according to the Hazen number expressed in the APHA unit, which was determined in the following manner.

In 200 cc of concentrated hydrochloric acid (hydrogen chloride content: 35% by weight) were dissolved 2.499 g of potassium chloroplatinate ($K_2PtCl_3$) and 2.00 g of crystalline cobalt chloride ($CoCl_2.6H_2O$), and the solution was diluted with distilled water to 1 liter to prepare a Hazen platinum-cobalt standard solution. The Hazen number of a solution obtained by diluting 1 cc of the standard solution with distilled water to a total volume of 1 liter was defined as 1 APHA and the Hazen number of a solution obtained by diluting X cc of the standard solution with distilled water to a total volume of 1 liter was defined as X APHA. A solution of 6 g of terephthalic acid crystals to be tested, dissolved in 120 cc of dimethylformamide, was prepared, and 100 cc of the solution was sampled into a color comparison tube. The color of the solution was compared with colors of several standard solutions of fixed APHA units filled in the same color comparison tubes in an amount of 100 cc, respectively, with naked eyes from above while palcing these color comparison tubes on white paper. The APHA unit of the sample solution was thus determined.

The content of 4-carboxybenzaldehyde in the terephthalic acid crystals was determined using Digital Polarograph PE-21 (tradename of a product manufactured by Yanagimoto Mfg. Co., Ltd., Japan) (half wave potential: $-1.24$ volts).

In Tables, "mother liquor content" means the reaction mixture mother liquor content, in % by weight, of the solvent acetic acid obtained by the solid-liquid separation of recovered terephthalic acid suspension.

EXAMPLE 1

The apparatus used was assembled in the following manner (see FIG. 1):

The reactor 1 was a titanium pressure reactor of 80 liters capacity and provided with reflux condensers 2 and 3, stirrer, heater, feed inlet, gas inlet and slurry outlet. The slurry outlet was connected to titanium tower 5 (14 cm diameter, 70 cm height, 7.5 liters net capacity) and further connected to titanium flash tank 7 of 50 liters capacity, bypassing preheater 14 and stirring tank 6.

Into reactor 1, were charged 30 kg of acetic acid, 25.4 g (0.020% by weight in terms of metal based on acetic acid) of cobalt acetate teterahydrate, 13.4 g (0.010% by weight in terms of metal based on acetic acid; 50% by weight in terms of metal based on cobalt metal) manganese acetate tetrahydrate, 9.7 g (0.15% by weight in terms of bromine atom) of hydrobromic acid (47% aqueous solution) and 2.1 g (7% by weight based on acetic acid) of water. Air was continuously introduced into the reactor through the gas inlet near the bottom. An acetic acid solution containing 17% by weight of para-xylene was continuously fed through the feed inlet to the reactor so that the average residence time in the reactor may become 2 hours. The rate of air feed was regulated so as to maintain the oxygen concentration in the exhaust gas within the range of 2 to 8% by volume. The reaction temperature was maintained at 196° C. and the reaction pressure at 20 kg/cm²G. The initial catalyst concentration was maintained by properly replenishing with fresh catalyst. The water content of the reacting mixture was maintained at 7% by weight by regulating the reflux from the reflux condenser.

The reaction mixture in the form of slurry (about 25% by weight terephthalic acid content) was withdrawn continuously by means of a slurry discharge device and continuously fed to the top of tower 5 at a rate of 90 liters/hour. The temperature in tower 5 was maintained at 190° C. or higher. Fresh acetic acid from acetic acid distillation dehydration tower 9, wherein acetic acid was dehydrated by distillation to a water content of 2% by weight, was preheated at 190° C. and fed continuously to the bottom of tower 5 at a rate of 87 liters/hour. The acetic acid was brought into countercurrent contact with the descending above-said suspension from the reactor and discharged as overflow from the top of tower. The ascending velocity of acetic acid containing water in the tower was 0.02 cm/second. The overflow contained 0.5% by weight of fine terephthalic acid crystals having a particle size of below several microns. The concentrations of cobalt and manganese were 0.019 and 0.010% by weight, respectively, based on solvent acetic acid, which were substantially the same as those in the reactor. The overflow was recycled to reactor 1 without any treatment.

The residence time of the terephthalic acid crystals in the tower was 5 minutes. The terephthalic acid suspension was withdrawn from the bottom of tower 5 at a rate of 90 liters/hour and fed continuously to flash tank 7, wherein the suspension was brought into vigorous boiling at atmospheric pressure, whereby the suspension was cooled to about 110° C. The cooled suspension was removed of the solvent acetic acid by solid-liquid separator 8 (in this example a centrifuge was used) to yield wet terephthalic acid crystals which were then dried. The cobalt content of the separated solvent acetic acid was found to be below the limit of detection, indicating that the terephthalic acid suspension withdrawn from tower 5 was substantially free from the reaction mother liquor.

After 10 hours of the abovementioned operation, when the operation was in the steady state, the product terephthalic acid showed constant quality shown in Table 1.

Examples 2 to 17; Comparative Examples 1 to 8

In Examples 2 to 17, the operation described in Example 1 was repeated, except that the rate of feeding the terephthalic acid suspension to tower 5 was nearly the same as the rate of withdrawing the suspension from the bottom; the rate of feeding the acetic acid containing water to the bottom of tower 5 was also the same as the rate of overflow from the top; the residence time of the terephthalic acid crystals in the tower and the ascending velocity of the acetic acid containing water were varied as shown in Table 1 by varying the rate of feeding the reaction mixture and the rate of feeding the acetic acid containing water; and the minimum temperature in tower 5 and the water content of acetic acid were varied as shown in Table 1 (the water content of acetic acid was varied by adding necessary amount of water to distillation-dehydrated acetic acid having a water content of 2% by weight). The results obtained were as summarized in Table 1 together with the results obtained in Example 1.

In Comparative Example 1 (no mother liquor replacement), the operation of Example 1 was repeated, except that the reaction mixture discharged from reactor 1 was continuously fed directly to flash tank 7, bypassing tower 5. In Comparative Examples 2 and 3, procedures of Examples 1 and 4, respectively, were repeated, except that the suspension discharged into flask tank 7 in Comparative Example 1 was fed to tower 5 in place of the reaction mixture.

Table 1

| | | Residence time of terephthalic acid crystals in tower (minute) | Minimum temperature of liquid in tower (°C.) | Water content of acetic acid containing water (weight % based on acetic acid) | Ascending velocity of acetic acid containing water in tower (cm/second) | Quality of recovered terephalic acid | | Mother liquor content and remarks |
|---|---|---|---|---|---|---|---|---|
| | | | | | | 4-carboxy-benzaldehyde (ppm) | Hazen (APHA) | |
| Example | 1 | 5 | 190 | 2 | 0.02 | 350 | 10 | <1% |
| | 2 | 2 | 189 | " | 0.02 | 450 | 11 | 5% |
| | 3 | 15 | 188 | " | 0.02 | 210 | 7 | |
| | 4 | 30 | 189½ | " | " | 180 | 5 | |
| | 5 | 60 | 190 | " | " | 175 | 6 | |
| | 6 | 10 | 191 | 4 | 0.03 | 295 | 9 | |
| | 7 | " | 190 | 2 | 0.05 | 270 | 8 | |
| | 8 | " | 191 | " | 0.10 | 240 | 7 | |
| | 9 | " | 190 | " | 0.50 | 200 | 6 | |
| | 10 | " | " | " | 3.50 | 210 | 6 | |
| | 11 | " | 191 | 12 | 0.03 | 285 | 8 | |
| | 12 | " | " | 3 | 0.007 | 495 | 10 | 9% |
| Example | 13 | 8 | 195 | 3 | 0.02 | 205 | 7 | |
| | 14 | " | 191 | " | " | 310 | 10 | |
| | 15 | " | 187 | " | " | 445 | 11 | |
| | 16 | 0.5 | 195 | 10 | 0.02 | 515 | 11 | |
| | 17 | 1 | 187 | 2 | " | 520 | 13 | 12% |
| Comparative Example | 1 | — | — | — | — | 950 | 18 | |
| | 2 | 5 | 190 | 2 | 0.02 | 860 | 16 | |
| | 3 | 30 | 189 | " | " | 655 | 15 | |
| | 4 | 10 | 185 | 4 | 0.03 | 530 | 12 | |
| | 5 | " | 170 | " | " | 875 | 17 | |
| | 6 | " | 160 | " | " | 940 | 19 | |
| | 7 | 15 | 188 | 2 | 0.004 | 505 | 11 | 15%; Discharge line tends to |

Table 1-continued

| Residence time of terephthalic acid crystals in tower (minute) | Minimum temperature of liquid in tower (°C.) | Water content of acetic acid containing water (weight % based on acetic acid) | Ascending velocity of acetic acid containing water in tower (cm/second) | Quality of recovered terephalic acid 4-carboxy-benzaldehyde (ppm) | Hazen (APHA) | Mother liquor content and remarks |
| --- | --- | --- | --- | --- | --- | --- |
| 8 | 10 | 191 | 3 | 5.5 | 500 | 12 | be blocked. Deterioration in yield and slurry forming ability. |

Examples 18 and 19; Comparative Example 9

Batchwise operation was conducted by providing automatic on-and-off valves in feeding and discharge lines for the terephthalic acid suspension, feeding line for hot acetic acid containing water, and discharge line for the recovered terephthalic acid suspension and repeating automatically the following sequence of steps: (1) feeding of the reaction mixture containing suspended terephthalic acid crystals to the contact tower, (2) termination of said feeding, (3) starting and continuation of continuous countercurrent contact by continuous feeding of hot acetic acid containing water to the bottom of tower and continuous discharge of the overflow from the top, (4) termination of the feeding and discharge of the hot acetic acid containing water, and (5) discharge of the terephthalic acid suspension to the flash tank. In step (3) conditions for the countercurrent contact were varied as shown in Table 2. The operation was otherwise the same as in Example 1. The tower was of the same type and same size as in Example 1. The results obtained were as shown in Table 2.

Table 2

| | Residence time of terephthalic acid crystals in tower (min.) | Minimum temperature of liquid in tower (°C.) | Water content of acetic acid containing water (wt.-% based on acetic acid) | Ascending velocity of acetic acid containing water in tower (cm/sec) | Quality of recovered terephthalic acid 4-Carboxy-benzaldehyde (ppm) | Hazen (APHA) |
| --- | --- | --- | --- | --- | --- | --- |
| Example 18 | 5 | 189 | 5 | 0.15 | 320 | 9 |
| Example 19 | 10 | 190 | 5 | 0.32 | 195 | 6 |
| Comparative Example 9 | 10 | 185 | 5 | 0.16 | 525 | 14 |

Example 20

The procedure of Example 11 was repeated, except that the acetic acid (12% water content) obtained by condensing vapor from the top of reactor was used for the acetic acid containing water. The results obtained were: 4-carboxybenzaldehyde contente: 250 ppm; Hazen number: 7 APHA.

Example 21

The procedure of Example 4 was followed, except that the oxidation temperature was 185° C. and the minimum temperature of the liquid is tower 5 was 179° C. The recovered terephthalic acid crystals showed a 4-carboxybenzaldehyde content of 400 ppm and a Hazen number of 9 APHA. When the reaction mixture was discharged directly into flash tank 7 without undergoing the countercurrent contact, the above values were 2250 ppm and 35, respectively.

Example 22

Procedure of Example 3 was repeated, except that a total of cobalt, manganese and bromine atom was 0.15% by weight based on acetic acid; water content of the reaction system was maintained at 7.5% by weight; reaction was carried out at 227° C. and 16 kg/cm$^2$G; the mean residence time of the reaction mixture in reaction 1 was 90 minutes; and the minimum temperature of the liquid in tower 5 was 220° C. The recovered terephthalic acid crystals showed a 4-carboxybenzaldehyde content of 195 ppm and a Hazen number of 5 APHA.

Example 23

Substantially the same operation as in Example 1 was repeated, except that 38.1 g (0.03% by weight in terms of cobalt metal based on acetic acid) of cobalt acetate tetrahydrate, 14.1 g (35% by weight in terms of manganese metal based on cobalt metal) of manganese acetate tetrahydrate, 9.7 g (0.15% by weight in terms of bromine atom) of hydrobromic acid (47% aqueous solution) and 2.4 kg (8% by weight based on acetic acid) of water were charged into reactor 1; reaction was carried out at 183° C., while feeding 0.3 mole of acetaldehyde for 1 mole of para-xylene; the residence time of the terephthalic acid crystals in tower 5 was 15 minutes; minimum temperature of the liquid in tower 5 was 178° C.; acetic acid (15% water content) obtained by the condensation of vapor from the reactor was used for the water-containing acetic acid; and the ascending velocity of said condensed acetic acid in the tower 5 was 0.03 cm/second. The recovered terephthalic acid crystals showed a 4-carboxybenzoldehyde content of 120 ppm and a Hazen number of 4 APHA, whereas when the countercurrent contat treatment was omitted, the above values were 460 ppm and 13 APHA, respectively.

Example 24

Substantially the same operation as in Example 1 was repeated, except that 1520 g (1.2% by weight in terms of cobalt metal based on acetic acid) of cobalt acetate tetrahydrate and 2.4 kg (8% by weight based on acetic acid) of water were charged; reaction temperature was 160° C.; the residence time of terephthalic acid crystals in contact tower was 10 minutes; the minimum temperature in the tower was 155° C.; acetic acid (15% water content) obtained by the condensation of vapor from the reactor was used for the water-containing acetic acid; and the ascending velocity of said acetic acid in the tower was 0.03 cm/second. The recovered terephthalic acid crystals showed a 4-carboxybenzaldehyde content of 195 ppm and a Hazen number of 8 APHA, whereas when the countercurrent contact treatment was omitted, the above values were 550 ppm and 15 APHA, respectively.

Example 25

A stainless steel (SUS 316L) stirring tank 6 of an internal volume of 110 liters (90 liters in net volume) was connected between tower 5 and flash tank 7 as shown in FIG. 1.

The procedure until the discharge of suspension from tower 5 was the same as in Example 1. The suspension discharged from the bottom of tower 5 at a rate of 90 liters/hour was continously fed to stirring tank 6. The temperature in the stirring tank was maintained above 185° C. The suspension from the stirring tank was continually discharged at a rate of 90 liters/hour into flash tank 7 and brought to rapid boiling at atmospheric pressure, whereby the suspension was cooled to about 110° C. The ascending velocity of the hot acetic acid containing water in tower 5 was 0.02 cm/second. The average residence time of the terephthalic acid crystals was 5 minutes in the tower and 60 minutes in stirring tank 6.

As in Example 1, the solvent acetic acid was removed from the cooled suspension by means of solid-liquid separator 8 (a centrifuge was used in this example) to obtain wet crystals of terephthalic acid which was then dried. The cobalt content of the separated solvent acetic acid was found to be below the limit of detection, indicating that the terephthalic acid suspension discharged from the tank was not contaminated with the reaction mother liquor. After 10 hours of continued operation, the operation was in steady state and the quality of the terephthalic acid crystals become constant. The results obtained were as shown in Table 3. As compared with the results obtained in Example 1 (not treatment in the stirring tank at elevated temperatures), the purification effect of the treatment in stirring tank was remarkable.

Examples 26 to 42; Comparative Examples 10 to 18

In Examples 26 to 42 and Comparative Examples 11 to 18, the residence time of terephthalic acid crystals and the ascending velocity of acetic acid containing water in tower 5 were varied as shown in Table 3 by varying the feeding rate of the reaction mixture and the feeding rate of acetic acid containing water, while maintaining the feeding of terephthalic acid crystals suspension to tower 5 and the discharge of suspension from the bottom at the same rate, as well as maintaining the feeding of acetic acid containing water to the bottom of tower 5 and the overflow from the tower at the same rate. The minimum temperature of the liquid in tower 5 and the water content of the acetic acid were varied as shown in Table 3 (the water content of the acetic acid was varied by adding a necessary amount of water to the distillation-dehydrated acetic acid containing 2% by weight of water). The residence time of terephthalic acid suspension in stirring tank 6 was varied as shown in Table 3 by changing the size of stirring tank 6 or liquid level in tank 6. The temperature in stirring tank 6 was regulated as shown in Table 3. The operation was otherwise the same as in Example 25. The results obtained were shown in Table 3 together with those obtained in Example 25.

In Comparative Example 10, the procedure of Example 25 was followed, except that the same suspension as that discharged into flash tank 7 in Example 1 was fed to tower 5 in place of the reaction mixture and treated under the conditions shown in Table 3.

Table 3

| Example No. | Residence time of terephthalic acid crystals in tower (minute) | Minimum temperature of liquid in tower (°C.) | Water content of acetic acid containing water (wt. % based on acetic acid) | Ascending velocity of acetic acid containing water in tower (cm/sec.) | Residence time of suspension in stirring tank (minute) | Temperature of liquid in stirring tank (°C.) | Quality of recovered terephthalic acid 4-Carboxybenzaldehyde (ppm) | Hazen (APHA) | Mother liquor content and remarks |
|---|---|---|---|---|---|---|---|---|---|
| 25 | 5 | 190 | 2 | 0.02 | 60 | 185 | 190 | 6 | <1% |
| 26 | 0.5 | 189 | " | 0.01 | " | 183 | 360 | 10 | 14% |
| 27 | 2 | 191 | 3 | 0.05 | " | 184 | 220 | 7 | |
| 28 | 10 | 190 | " | 0.10 | " | 185 | 180 | 6 | |
| 29 | 5 | " | " | 0.03 | 7 | 182 | 300 | 8 | |
| 30 | " | 187 | " | " | 30 | 181 | 230 | 7 | |
| 31 | " | " | " | " | 120 | 182 | 170 | 5 | |
| 32 | " | " | " | " | 180 | " | 160 | 3 | |
| 33 | 3 | " | 2 | 0.007 | 60 | 180 | 350 | 10 | 18% |
| 34 | " | 190 | " | 0.80 | 30 | 181 | 200 | 7 | |
| 35 | " | " | " | 3.90 | " | 181 | 210 | 7 | |
| 36 | 5 | 193 | " | 0.10 | 60 | 190 | 170 | 5 | |
| 37 | 5 | 193 | 2 | 0.10 | 60 | 200 | 160 | 5 | |
| 38 | " | " | " | " | " | 215 | 150 | 7 | |
| 39 | 1.5 | " | " | " | 120 | 200 | 120 | 3 | |
| 40 | 2 | 188 | 12 | 0.03 | 60 | 182 | 210 | 7 | |
| 41 | 3 | 190 | 10 | 0.01 | 60 | 185 | 205 | 7 | |
| 42 | 6 | 189 | 3 | 0.20 | " | 225 | 145 | 11 | |
| Comparative Example No. | | | | | | | | | |
| 10 | 5 | 190 | 2 | 0.02 | 60 | 185 | 250 | 8 | |
| 11 | 0.3 | 189 | " | " | 60 | 181 | 510 | 15 | 24% |
| 12 | 2 | 178 | 3 | 0.03 | " | 173 | 450 | 13 | |
| 13 | " | 170 | " | " | " | 165 | 600 | 16 | |

Table 3-continued

| | Residence time of terephthalic acid crystals in tower (minute) | Minimum temperature of liquid in tower (°C.) | Water content of acetic acid containing water (wt. % based on acetic acid) | Ascending velocity of acetic acid containing water in tower (cm/sec.) | Residence time of suspension in stirring tank (minute) | Temperature of liquid in stirring tank (°C.) | Quality of recovered terephthalic acid | | Mother liquor content and remarks |
|---|---|---|---|---|---|---|---|---|---|
| | | | | | | | 4-Carboxy-benzaldehyde (ppm) | Hazen (APHA) | |
| 14 | 4 | 186 | " | 0.20 | 80 | 172 | 430 | 13 | |
| 15 | 2 | 190 | " | 0.03 | 3 | 182 | 405 | 11 | |
| 16 | 10 | 188 | 2 | 0.004 | 30 | 180 | 495 | 10 | Discharge line tends to be blocked. |
| 17 | 10 | 190 | 3 | 5.5 | 30 | 184 | 440 | 12 | Marked decreased in yield and deteriorration in slurry-forming ability. |
| 18 | 1 | 188 | 2 | 0.01 | 60 | 175 | 450 | 12 | 21% |

Example 43

Example 40 was repeated, except that acetic acid (12% water content) obtained by condensing the vapor from the top of reactor was used for the water-containing acetic acid. The product terephthalic acid showed a 4-carboxybenzaldehyde content of 190 ppm and a Hazen number of 6 APHA.

Example 44

Example 26 was repeated, except that 3 trays were provided in the continuous countercurrent contact tower as shown in FIG. 2. The recovered terephthalic acid crystals showed a 4-carboxybenzaldehyde content of 250 ppm and a Hazen number of 8 APHA. The acetic acid separated from the recovered terephthalic acid suspension contained 5% by weight of the reaction mixture mother liquor.

What is claimed is:

1. In a process for recovering highly pure terephthalic acid from a reaction mixture containing terephthalic acid crystals suspended in mother liquor obtained by liquid-phase oxidation of a para-substituted aromatic compound in an acetic acid with a gas containing molecular oxygen in the presence of oxidizing catalyst under such condition that the reaction temperature is 100° to 250° C. and the water content of the reaction system is 2 to 15% by weight based on said acetic acid, the improvement which comprises, without cooling and without subjecting to solid-liquid separation, feeding said hot reaction mixture suspension to a single tower, wherein the suspension is brought into continuous countercurrent contact with acetic acid containing water ascending at a linear velocity of 0.005 to 5 cm/second at a temperature not lower than the oxidation temperature by more than 10° C., the average residence time of terephthalic acid crystals in the tower being 30 seconds or more, thereby to replace the mother liquor of the suspension with said acetic acid containing water recovering said mother liquor as the overflow effluent from the tower, while discharging as the underflow effluent the resulting suspension of terephthalic acid crystals in substantially pure acetic acid and separating highly pure terephthalic acid crystals from the suspension.

2. A process according to claim 1, wherein the average residence time of the terephthalic acid crystals in the continuous countercurrent contact tower is 2 minutes or more.

3. A process according to claim 1, wherein the average residence time of the terephthalic acid crystals in the continuous countercurrent contact tower is 10 to 30 minutes.

4. A process according to claim 1, wherein the oxidizing catalyst is a combination of a cobalt compound, a manganese compound and a bromide compound.

5. A process according to claim 1, wherein the oxidation catalyst is a combination of a cobalt compound, a manganese compound, a bromide compound and acetaldehyde.

6. A process according to claim 1, wherein the para-substituted aromatic compound is a para-dialkylbenzene.

7. A process according to claim 6, wherein the para-dialkylbenzene is para-xylene.

8. A process according to claim 1, wherein the gas containing molecular oxygen is air.

9. A process according to claim 1, wherein the oxidation temperature is 170° to 220° C.

10. A process according to claim 1, wherein the water content of the reaction system is 3 to 9% by weight based on acetic acid.

11. A process according to claim 1, wherein the temperature inside the continuous countercurrent contact tower is higher than the reaction temperature.

12. A process according to claim 1, wherein the ascending velocity of the acetic acid containing water in the continuous countercurrent contact tower is 0.01 to 0.5 cm/second.

13. A process according to claim 1, wherein the water content of the acetic acid containing water is 10 to 20% by weight.

14. A process according to claim 13, wherein the acetic acid containing water is a reactor overhead condensate obtained by condensing the vapor generated from the oxidation reactor so that the water content of the condensate may become 10 to 20% by weight.

15. A process according to claim 1, wherein about 90% by weight or more of the mother liquor contained in the reaction mixture in which terephthalic acid crystals are suspended are replaced with countercurrently contacting acetic acid containing water and are recovered as the overflow from the tower, while the terephthalic acid crystals are recovered as the underflow in the form of a suspension in acetic acid containing water not containing more than 10% by weight of the reaction mixture mother liquor.

16. A process according to claim 1, wherein the continuous countercurrent contact tower is provided with at least one tray having at least one aperture with a minimum clearance of 5 mm or more.

17. A process according to claim 16, wherein the total aperture area of each tray is 5 to 50% of the cross-sectional area of the continuous countercurrent contact tower.

18. A process according to claim 1, wherein the overflow of the contact tower is recycled back to the reactor.

19. A process according to claim 1, wherein sending the underflow suspension to a stirring tank wherein the suspension is allowed to stay at a temperature not lower than the inside temperature of the tower by more than 10° C., and separating highly pure terephthalic acid crystals from the suspension.

20. A process according to claim 19, wherein the reaction mixture suspension is brought into continuous countercurrent contact with the ascending acetic acid containing water while the residence time in tower of the terephthalic acid being maintained at 30 seconds to 10 minutes, whereby about 80% by weight or more of the mother liquor in said suspension is replaced by said acetic acid containing water and recovered as the overflow from the tower while the terephthalic acid crystals suspended in acetic acid containing water and containing not more than about 20% by weight of said mother liquor are discharged as underflow into a stirring tank and allowed to stay there at a temperature not lower than the temperature in the countercurrent contact tower by more than 10° C., the residence time in the stirring tank being from 5 minutes to 180 minutes.

21. A process according to claim 20, wherein the average residence time of the terephthalic acid crystals in the continuous countercurrent contact tower is from 30 seconds to 2 minutes and the average residence time of said crystals in the stirring tank is from 60 to 180 minutes.

22. A process according to claim 20, wherein the suspension of terephthalic acid crystals in acetic acid containing water is retained in the stirring tank at a temperature higher than the oxidation temperature and lower than 225° C.

23. A process according to claim 20, wherein before being fed to the stirring tank, the underflow from the continuous countercurrent contact tower is admixed with about 50 to about 300% by weight (based on acetic acid in said underflow) of hot acetic acid containing water.

* * * * *